United States Patent [19]

Vancaillie

[11] Patent Number: 5,788,694

[45] Date of Patent: Aug. 4, 1998

[54] SELF-GUIDING ELECTRODE FOR TISSUE RESECTION

[76] Inventor: Thierry G. Vancaillie, 133 Pin Oak Forest, San Antonio, Tex. 78232

[21] Appl. No.: 585,989

[22] Filed: Jan. 16, 1996

Related U.S. Application Data

[63] Continuation-in-part of Ser. No. 164,107, Dec. 8, 1993, Pat. No. 5,486,173.

[51] Int. Cl.⁶ .................................................. A61B 17/39
[52] U.S. Cl. .................................................. 606/45; 606/46
[58] Field of Search .................................. 606/45, 46, 48, 606/49, 52

[56] References Cited

U.S. PATENT DOCUMENTS

| | | | |
|---|---|---|---|
| 4,116,198 | 9/1978 | Roos | 606/46 |
| 5,196,011 | 3/1993 | Korth et al. | 606/46 |

FOREIGN PATENT DOCUMENTS

| | | | |
|---|---|---|---|
| 419235 | 3/1991 | European Pat. Off. | 606/45 |
| 1548389 | 10/1968 | France | 606/46 |

OTHER PUBLICATIONS

C.J.G. Sutton, et al., "Endometrial Resection", 'Endometrial Ablation', Churchill Livingstone, 1993, pp. 91–131.

*Primary Examiner*—Lee S. Cohen
*Attorney, Agent, or Firm*—Fish & Richardson P.C.

[57] ABSTRACT

An electrode having at least one self-guiding surface (a tissue skid) for use in electrical tissue resection. Self-guiding forces are applied substantially perpendicular to the longitudinal axis of the electrode, and/or rotationally about the longitudinal axis. Forces sufficient to compensate in part for errors in cutting tip placement are produced by tissue pressure acting on one or more convex tissue skids. Optional tissue cutting tips for the electrode are configured to enhance heat transfer from the cutting tip by external fluid flow around the cutting tip, to improve heat transfer within the cutting tip through use of heat transfer fluids and/or heat-conducting solids, and/or to cool the cutting tip by expansion of a compressed cooling fluid through an orifice within a hollow portion of the cutting tip.

15 Claims, 2 Drawing Sheets

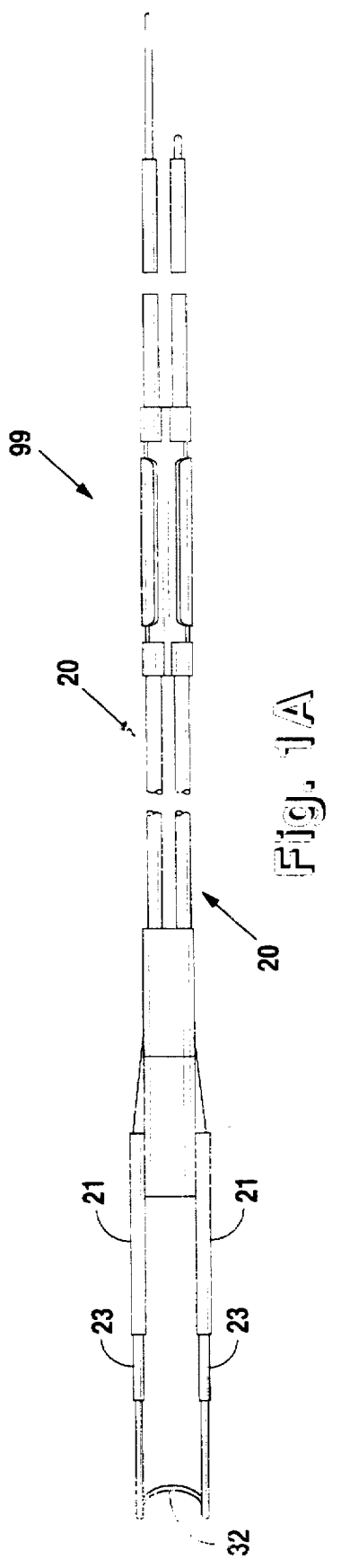
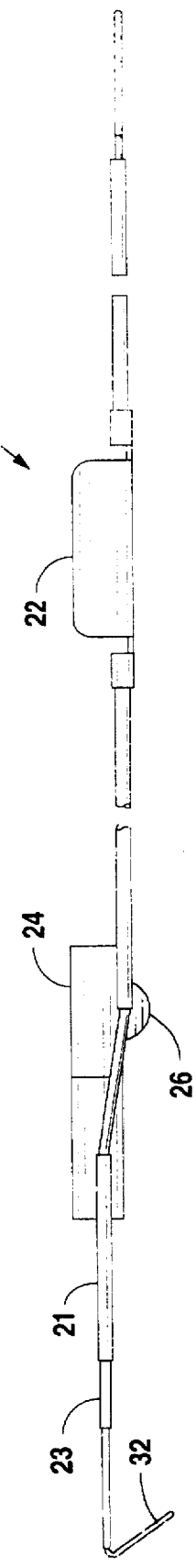
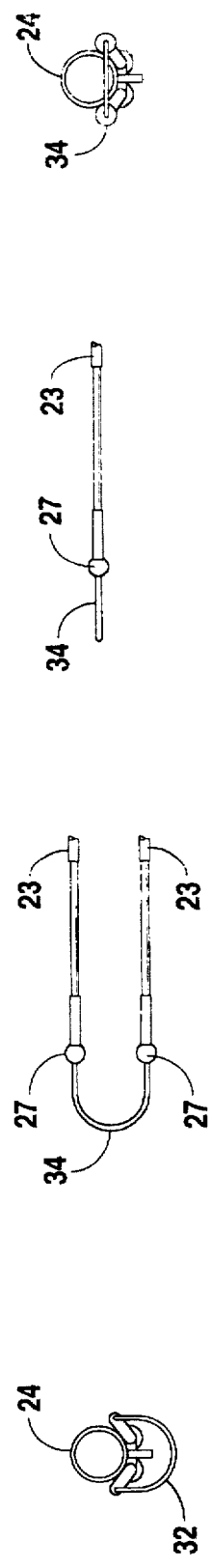

SELF-GUIDING ELECTRODE FOR TISSUE RESECTION

This application is a continuation-in-part of application Ser. No. 08/164,107, filed Dec. 8, 1993, now U.S. Pat. No. 5,486,173.

BACKGROUND

1. Field of the Invention

The invention relates to methods and apparatus for electrical resection of tissue.

2. Endoscopic Tissue Resection

Surgical tissue resection deep within body cavities may be performed either under direct vision or endoscopically with the aid of electrodes which are elongated (along a longitudinal axis) and thin enough to be inserted directly into the incision or placed through an endoscope. Notwithstanding their relatively small transverse dimensions, these electrodes comprise at least one insulated electrical conductor and commonly have two. Monopolar electrodes, which in use rely on a return current path through the patient's body, may have only one or a plurality of insulated electrical conductors. Bipolar electrodes, in contrast, provide a return current path through one or more insulated electrical conductors; hence bipolar electrodes commonly have two insulated conductors. Electrodes preferably additionally comprise an electrically energized electrode cutting loop tip (generally a wire which may be straight or bent into a curved, circular or oval shape). While electrodes having two insulated conductors may be either monopolar or bipolar, they typically have circular or oval wire cutting loops and do not require substantial currents to pass through the patient's body.

Designed to be manipulated from outside a patient's body through a relatively small orifice or incision, an electrode cutting tip intended for endoscopic surgery may deflect significantly under the influence of relatively small lateral (bending) forces substantially perpendicular to the electrode's longitudinal axis or torsional (twisting) forces which act around the electrode's longitudinal axis. The surgeon counteracts any unintended deflections and otherwise guides the tip along a desired cutting plane by applying corrective forces while viewing the cutting tip movement through the endoscope.

Precise guidance of an electrode cutting tip along a predetermined cutting plane requires exceptional skill because of the restricted visibility offered by an endoscope or small incision, as well as the relatively great distances separating the surgeon's hands from the tissue being resected. This is particularly true during electrical tissue resection because relatively small forces are sufficient to alter the path of an electrode cutting tip cutting through tissue. Such small forces, acting on the cutting tip at a point substantially distant from the surgeon's hand, are difficult for the surgeon to sense.

An additional problem common to many electrode tips is overheating. While tissue in contact with the tip is ablated and/or transected, the tip should preferably remain relatively cool to prevent the buildup of coagulated proteins and/or charred tissue debris. Accumulations of debris on an electrode tip can impede electrical current flow and decrease the efficiency of tissue ablation, which slows recovery and predisposes the patient to post-operative complications.

SUMMARY OF THE INVENTION

The present invention relates to methods and apparatus for tissue resection with electrically-energized electrodes which are self-guiding and which preferably comprise tissue cutting tips which themselves comprise cooling means. Cooling means provide for increased heat transfer between cutting tips and a cooling fluid which is preferably directed around and/or within the cutting tips. Because electrodes of the present invention have at least one self-guiding construction feature, they tend to be more easily controllable by a surgeon. Self-guiding electrodes of the present invention achieve and/or maintain alignment or spacing of an electrode tissue cutting tip (e.g., a tissue-cutting loop) with respect to one or more tissue surfaces, and at least partially compensate for small errors in forces applied to direct an electrode tissue cutting tip as it moves through tissue.

An electrode of the present invention thus comprises at least one longitudinal electrical conductor which is insulated to prevent undesired electrical contact and which has a proximal end and a distal end. The electrode further comprises a tissue cutting tip coupled to at least one of the electrical conductors proximate its distal end. Additionally, at least one tissue skid having an at least partially convex surface (or a portion thereof) is present and may be coupled to at least one of the electrical conductors. One or more of these conductors may optionally be hollow to provide means for carrying cooling fluid to and/or away from a cutting tip which comprises cooling means. An electrode tissue cutting tip comprising cooling means (comprising, for example, a linking electrical conductor coupled to a structure of relatively larger cross-sectional area) is coupled to one or two insulated longitudinal conductors carrying electrical current from outside the body by loop coupling means which include, for example, welded or brazed junctions, screw terminals, snap-fit or friction-fit connectors. Thus, an electrode cutting tip of the present invention may be detachable (e.g. with screw terminals, snap-fit or friction-fit connectors) or substantially non-detachable (e.g., with brazed or welded connections) from the remaining portion of an electrode.

Self-guiding features of electrodes of the present invention relate to one or more at least partially convex tissue interfaces (tissue skids) coupled to the electrode, each interface being capable of exerting lateral forces (that is, forces substantially perpendicular to the electrode's longitudinal axis) and in some embodiments rotational forces (that is, forces substantially about the electrode's longitudinal axis) on the electrode as the skid contacts tissue. In preferred embodiments, a tissue interface may take the form of a substantially nonconductive skid coupled to the electrode (e.g., coupled to an electrode longitudinal conductor, a tissue cutting tip, or to a longitudinal conductor and cutting tip simultaneously). The tissue skid is formed by a protuberance which has a rounded (or doubly convex) three-dimensional surface (such as that of a sphere or ellipsoid or a portion thereof), being substantially smooth so as to slide over a tissue surface, and having sufficient surface area to transmit sufficient alignment force (arising from tissue pressure on the skid) to the electrode from the tissue to maintain a substantially fixed desired spacing of at least a portion of the electrode with respect to the tissue surface.

Tissue skids may have a low-friction surface (such as Teflon®) and also have rounded edges and at least a partially convex configuration with respect to the tissue surface to facilitate sliding without materially deforming or damaging the tissue surface. Tissue skids may be substantially electrically non-conductive or substantially electrically conductive (that is, generally, metallic in nature), but insulated from one or more of the longitudinal electrical conductors of an electrode as necessary to prevent undesired electrical current flow between different parts of the electrode and/or between the electrode and any portion of the patient's and/or the surgeon's body. A cutting tip which comprises cooling means, which itself comprises either a substantially solid or substantially hollow structure of relatively larger cross-sectional area coupled to a linking electrical conductor, may incorporate one or more (conductive or nonconductive) tissue skids in substantially spherical or ellipsoidal shapes which are part of the relatively larger cross-sectional area.

In embodiments of the present invention which comprise a cutting tip which itself comprises cooling means, the cooling means may include various combinations of components and construction features to facilitate the movement of heat from a cutting tip to a cooling fluid. The cooling fluid may be liquid or gas and is preferably directed to flow around and/or within the cooling means portion of the cutting tip. For example, irrigation fluid may be directed to flow over and around a cutting tip which comprises augmented heat transfer surface means (including a plated, coated, roughened, grooved, finned, channeled or perforated surface). The surface area available for heat transfer is increased by incorporating a hollow or solid structure of relatively larger cross-sectional area within and/or coupled to the linking electrical conductor of a tissue cutting tip. The hollow or solid structure preferably has an overall rounded shape which may be, for example, substantially that of a right circular cylinder or substantially that of an ellipsoid. Portions of the otherwise substantially smooth surface of the structure may comprise augmented heat transfer surface means.

Substantially solid cutting tip cooling means may comprise a relatively high thermal conductivity metal (such as copper or silver) as a medium to more efficiently transfer heat from a tissue interface to portions of the cutting tip which can be exposed to a flow of cooling fluid. Substantially hollow cutting tip cooling means may contain an effective amount of a volatile fluid medium useful in transferring heat from hotter portions of the cutting tips (such as tissue interfaces having a relatively high electrical current density) to cooler (preferably actively cooled) portions of the cutting tips. Cutting tip cooling means may also incorporate one or more fluid expansion orifices from which compressed liquids and/or gases are permitted to expand and cool the cutting tips. Expanded gas (for example, carbon dioxide) may be released through one or more outlets in the cutting tips or, preferably, conducted away from the cutting tips by an enclosed gas collection system.

In addition to various embodiments of electrodes, the present invention includes tissue cutting tips comprising cooling means, methods for making them and methods for cooling them.

BRIEF DESCRIPTION OF THE DRAWINGS

FIG. 1A schematically illustrates a plan view of a two-conductor electrode with an acute angle tissue cutting loop tip and a tissue skid coupled to the conductors.

FIG. 1B schematically illustrates a side elevation of the two-conductor electrode of FIG. 1.

FIG. 1C schematically illustrates a front elevation of the two-conductor electrode of FIG. 1.

FIG. 1D schematically illustrates a plan view of the distal portion of a two-conductor electrode with a coplanar zero angle tissue cutting loop.

FIG. 1E schematically illustrates a side elevation of the two-conductor electrode portion of FIG. 1D.

FIG. 1F schematically illustrates a front elevation of a two-conductor electrode comprising the portion of FIG. 1D.

DETAILED DESCRIPTION

Figure 1G:
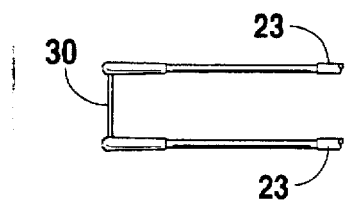
FIG. 1G schematically illustrates a plan view of the distal portion of a two-conductor electrode with a right angle tissue cutting loop.
Figure 1H:
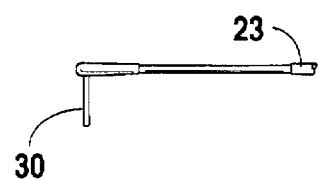
FIG. 1H schematically illustrates a side elevation of the two-conductor electrode portion of FIG. 1G.
Figure 1I:
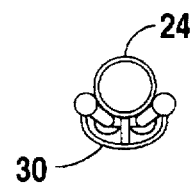
FIG. 1I schematically illustrates a front elevation of a two-conductor electrode comprising the portion of FIG. 1G.

Preferred embodiments of the invention include an electrode 99 which comprises at least one longitudinal electrical conductor 20 having a proximal end and a distal end as schematically illustrated in FIGS. 1(A–I). The electrode 99 further comprises a tissue cutting tip (itself comprising a linking electrical conductor such as the tissue cutting loop 32) coupled to at least one of the longitudinal electrical conductors 20 proximate the conductor's distal end. An electrode further comprises at least one at least partially convex tissue skid 26, which may be coupled to at least one electrical conductor 20.

Tissue skids may be metallic (that is, electrically conductive), in which case each such tissue skid is electrically insulated to prevent inadvertent electrical contact with electrical conductors of the electrode. Skids may also be electrically nonconductive so that preventive electrical insulation is unnecessary. Electrical insulation 23 is optionally part of a longitudinal electrical conductor 20 where needed to prevent undesired electrical contact, and note that an outer metal tube 21 may be fitted over the insulation 23 for added stiffness and/or for firm coupling (as by molding, welding or soldering) to a resectoscope guide tube or analogous substantially rigid member to form a stabilizer assembly.

Alignment force is transmitted from tissue contacted by a skid to the skid, and through the skid to the electrode via at least one skid coupling means. Skid coupling means include, for example, snap-fit, friction-fit, press-fit, clip-on, swaged-on, molded-on, molded-in, or adhesively-attached couplings, and the position of a skid coupling means on an electrode may be either adjustable or substantially non-adjustable in use.

Tissue skids may be coupled to any portion of an electrode where application of lateral forces is desired. In preferred embodiments, a skid may be coupled to both of two substantially parallel and insulated longitudinal electrical conductors adjacent to the distal ends of the conductors (that is, adjacent to a tissue cutting tip as in FIG. 1D) or proximal to this location as in FIG. 1B.

Preferred sizes for contact areas of tissue skids may be determined depending on several factors, including the type of tissue to be resected, the size of the cutting tip, and the magnitude of lateral forces desired. Skids exert reaction forces on tissue which are proportional to the lateral forces exerted on the electrode to which they are coupled. Effective positional control of the electrode therefore requires that pressures applied to tissues not cause significant displacement of the tissue adjacent to a skid. For example, electrodes suitable for resection of endometrial tissue may have two skids within about 30 mm of a cutting tip with a total minimum skid tissue contact area preferably within a range of about 4 to 100 mm$^2$, depending in part on actual skid-tip distance. Skids immediately adjacent to a cutting tip in this application preferably have individual surface areas of about 3 to about 10 mm$^2$.

Whether electrically conductive or nonconductive, tissue skids 27 may be located near the distal ends of the longitudinal electrical conductors, substantially adjacent to the tissue cutting tip (as in FIG. 1D). In this case, a preferred form for the skids would be substantially spherical (as schematically illustrated), with the linking conductor of the cutting tip protruding through at least one skid. However, skids may also be (or may instead be) located at a support point proximal to the cutting tip, preferably about two-thirds to three-fourths of the distance from the proximal to the distal end of the electrode. If the electrode comprises two longitudinal conductors, they may be coupled by a stabilizer assembly, the stabilizer assembly preferably being located at the above support point and thus furnishing a convenient location for coupling one or more skids to the electrodes. Note that a skid may also comprise the end portion 39 of cooling means 36 as shown in FIG. 2C. This end portion may be conductive or a layer of insulation contiguous with that of longitudinal conductor 20,20',20" may extend over end portion 39 to make the resulting skid electrically nonconducting.

In the electrode embodiments schematically illustrated in FIGS. 1(A-I), the stabilizer assembly comprises a guide tube 24 through which the distal end of an endoscope may be inserted. When the endoscope is a rigid tube resectoscope (not shown), a portion of the rigid tube proximal to that within the guide tube 24 may by further stabilized with respect to the electrode by its reversible insertion in the spring guide clip 22.

Figure 2A:
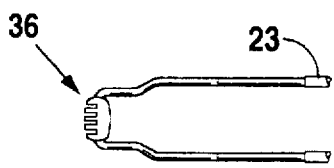
FIG. 2A schematically illustrates a plan view of the distal portion of a two-conductor electrode with a tissue cutting loop comprising grooved cooling means.
Figure 2B:
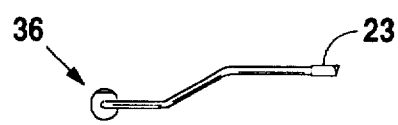
FIG. 2B schematically illustrates a side elevation of the two-conductor electrode portion of FIG. 2A.
Figure 2C:
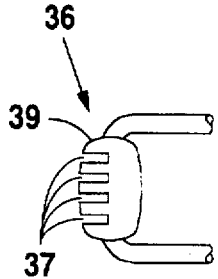
FIG. 2C schematically illustrates a detailed plan view of the distal portion of the two-conductor electrode portion of FIG. 2A.

A resectoscope (not shown) adapted for use with electrodes of the present invention would typically comprise a channel to allow the introduction of a (typically) nonconducting irrigation fluid (which also serves as a cooling fluid) to the vicinity of a tissue cutting tip comprising cooling means (see FIGS. 2(A-C)). Note that fluid flowing from the end of a resectoscope inserted within guide tube 24 will tend to strike and flow around cooling means 36. In particular, fluid flowing over the surface of cooling means 36 would be exposed to the increased surface area represented by grooves 37, and heat transfer from cooling means 36 to the fluid (not shown) would be increased as a function of the increased surface area. Analogous increases in heat transfer may be obtained if grooves 37 are replaced or supplemented with other augmented heat transfer surface means, as described above.

Figure 3:
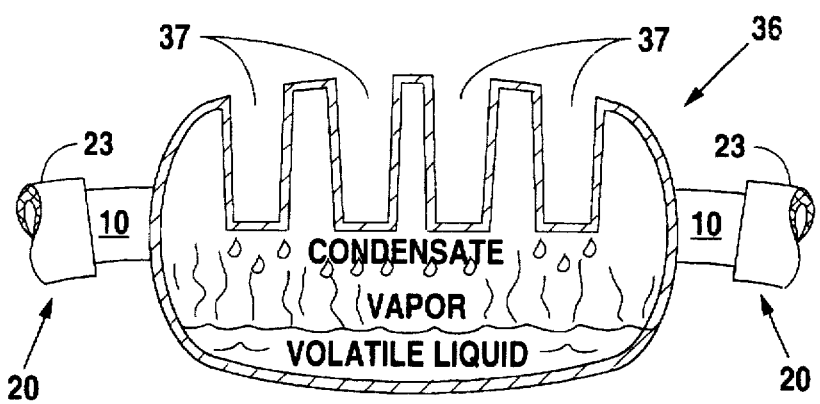
FIG. 3 schematically illustrates portions of the linking electrical conductor and the substantially hollow structure of a tissue cutting tip comprising cooling means that include a heat transfer fluid.

Heat transfer from cooling means 36 to a cooling fluid flowing around cooling means 36 may also be increased if cooling means 36 comprises relatively better heat conductors (such as the metals copper and silver). To even further enhance total heat transfer from cooling means 36, a heat transfer fluid may be incorporated in a hollow portion of cooling means 36 as schematically illustrated in FIG. 3. Such a heat transfer fluid would preferably be one which is relatively easily vaporized at the temperatures which electrosurgery would induce in the portions of cooling means 36 in contact with tissue being electrically ablated. The fluid would also preferably be nonflammable and relatively nontoxic in the quantities found in cooling means 36, and be easily condensed at the temperature of cooling fluid which may be flowed over cooling means 36. Such a fluid might be chosen from the various liquid halogenated anesthetic agents approved for use in humans (such as halothane, enflurane, desflurane or sevoflurane).

FIG. 3 schematically illustrates the preferably continuous process of evaporation of cooling fluid (a cooling process), and cooling fluid vapor condensation, which is a heat transfer process to the grooves 37 and thus to whatever external cooling agent (not shown) is in contact with the grooves 37. Note that in FIG. 3, cooling means 36 is electrically connected to longitudinal electrical conductors 20, each comprising a central metallic conductor 10 (such as copper or nickel silver) with appropriate insulation 23 sufficient to prevent inadvertent electrical contact with the central metallic conductor 10. Note also that the illustrated grooves 37 are only examples of the variety of augmented heat transfer surface means which can be used to enhance heat removal from cooling means 36.

Figure 4:
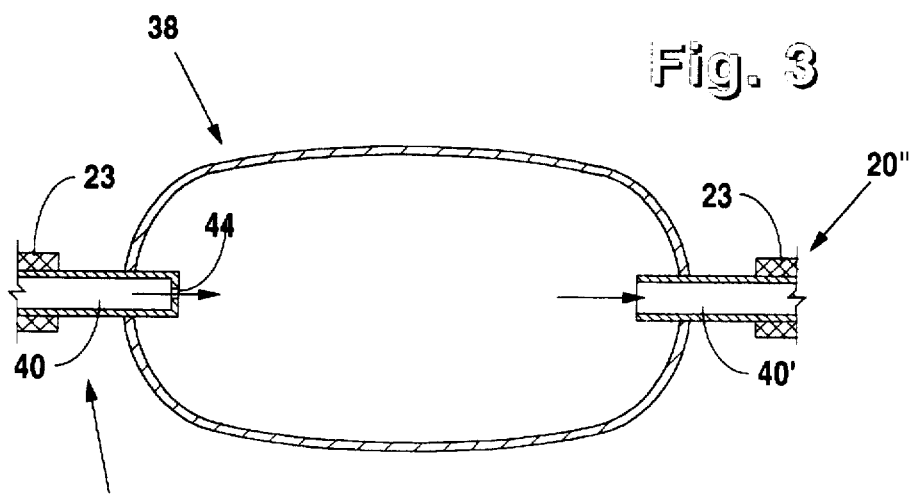
FIG. 4 schematically illustrates portions of the linking electrical conductor and the substantially hollow structure of a tissue cutting tip comprising cooling means that include an orifice for expansion of a compressed fluid.

Another way of removing heat from a tissue cutting tip with cooling means is by use of cooling means 38, as schematically illustrated in FIG. 4. In contrast, to cooling means 36, which is designed to facilitate heat transfer to an externally applied cooling fluid, cooling means 38 is designed to facilitate heat transfer to an internal cooling fluid which is subsequently removed from cooling means 38. The internal cooling fluid (for example, pressurized carbon dioxide) is admitted to cooling means 38 through a hollow central electrical conductor 40 (a part of longitudinal electrical conductor 20') which is electrically insulated as above with insulation 23. The compressed cooling fluid (not shown) is allowed to expand through orifice 44 and thus to cool. The cooled expanded cooling fluid (not shown) then absorbs heat by contact with the interior surface of cooling means 38 and exits (preferably) through an outlet comprising a hollow central electrical conductor 40' (a part of longitudinal electrical conductor 20"). Note that where embolization of expanded cooling fluid would not pose a significant clinical risk, one or more outlets from the cooling means may be provided in the region of electrosurgery.

What is claimed is:

1. An electrode comprising:

a first longitudinal member, having a proximal end and a distal end;

a second longitudinal member, having a proximal end and a distal end;

a tissue cutting tip coupled to the first longitudinal member proximate the distal end thereof and coupled to the second longitudinal member proximate the distal end thereof at least one of the first longitudinal member and second longitudinal member including a conductor electrically coupled to the tissue cutting tip;

a first tissue skid, electrically nonconductive and at least partially convex, and coupled to the first longitudinal member, proximally of the tissue cutting tip; and a second tissue skid, electrically nonconductive and at least partially convex, and coupled to the second longitudinal member proximally of the tissue cutting tip.

2. The electrode of claim 1 wherein the first tissue skid comprises a first doubly convex protuberance and the second tissue skid comprises a second doubly convex protuberance.

3. The electrode of claim 2 wherein the first doubly convex protuberance has a substantially spherical surface portion and the second doubly convex protuberance has a substantially spherical surface portion.

4. The electrode of claim 1 wherein the tissue cutting tip comprises a tissue cutting loop.

5. The electrode of claim 4 wherein the tissue cutting loop is substantially coplanar with the first longitudinal member and the second longitudinal member.

6. The electrode of claim 4 wherein the tissue cutting loop is at a right angle to the first longitudinal member and the second longitudinal member.

7. A tissue cutting electrode for applying a tissue cutting current along a current path to cut a tissue of a patient's body, comprising:

a first longitudinal member, having a proximal end and a distal end;

a second longitudinal member, having a proximal end and a distal end;

a tissue cutting tip coupled to the first longitudinal member proximate the distal end thereof and coupled to the second longitudinal member proximate the distal end thereof, at least one of the first longitudinal member and second longitudinal member including a conductor electrically coupled to the tissue cutting tip;

a first tissue skid, at least partially convex, and coupled to the first longitudinal member, proximally of the tissue cutting tip and configured so as to prevent flow of the current through the first tissue skid; and a second tissue skid, at least partially convex, and coupled to the second longitudinal member, proximally of the tissue cutting tip and configured so as to prevent flow of the current through the second tissue skid.

8. The electrode of claim 7 wherein the first tissue skid comprises a first doubly convex protuberance and the second tissue skid comprises a second doubly convex protuberance.

9. The electrode of claim 8 wherein the first doubly convex protuberance has a substantially spherical surface portion and the second doubly convex protuberance has a substantially spherical surface portion.

10. The electrode of claim 7 wherein the first tissue skid and the second tissue skid are nonconductive.

11. The electrode of claim 7 wherein the tissue cutting tip comprises a tissue cutting loop.

12. The electrode of claim 11 wherein the tissue cutting loop is substantially coplanar with the first longitudinal member and the second longitudinal member.

13. The electrode of claim 11 wherein the tissue cutting loop is at a right angle to the first longitudinal member and the second longitudinal member.

14. A tissue cutting electrode for applying a tissue cutting current along a current path to cut a tissue of a patient's body, comprising:

a first longitudinal member, having a proximal end and a distal end;

a second longitudinal member, having a proximal end and a distal end;

a tissue cutting tip coupled to the first longitudinal member proximate the distal end thereof and coupled to the second longitudinal member proximate the distal end thereof, at least one of the first longitudinal member and second longitudinal member including a conductor electrically coupled to the tissue cutting tip;

a first tissue skid, having a substantially spherical surface portion, and coupled to the first longitudinal member; and a second tissue skid, having a substantially spherical surface portion, and coupled to the second longitudinal member.

15. A tissue cutting electrode for applying a tissue cutting current along a current path to cut a tissue of a patient's body, comprising:

a first longitudinal member, having a proximal end and a distal end;

a second longitudinal member, having a proximal end and a distal end;

a tissue cutting tip coupled to the first longitudinal member proximate the distal end thereof and coupled to the second longitudinal member proximate the distal end thereof, at least one of the first longitudinal member and second longitudinal member including a conductor electrically coupled to the tissue cutting tip;

a first tissue skid formed as a protuberance on the first longitudinal member and configured so as to prevent flow of the current through the first tissue skid; and a second tissue skid formed as a protuberance on the second longitudinal member, the second tissue skid formed discretely from the first tissue skid and configured so as to prevent flow of the current through the second tissue skid.

* * * * *